United States Patent
Breuil et al.

(10) Patent No.: US 10,646,860 B2
(45) Date of Patent: *May 12, 2020

(54) CATALYTIC COMPOSITION COMPRISING NICKEL, A PHOSPHINE-TYPE LIGAND AND A LEWIS BASE, AND USE THEREOF IN AN OLEFIN OLIGOMERISATION METHOD

(71) Applicant: IFP Energies Nouvelles, Rueil-Malmaison (FR)

(72) Inventors: Pierre-Alain Breuil, Lyons (FR); Olivia Chaumet-Martin, Brignais (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,725

(22) PCT Filed: Dec. 13, 2016

(86) PCT No.: PCT/EP2016/080737
§ 371 (c)(1),
(2) Date: Jun. 15, 2018

(87) PCT Pub. No.: WO2017/102689
PCT Pub. Date: Jun. 22, 2017

(65) Prior Publication Data
US 2019/0001317 A1   Jan. 3, 2019

(30) Foreign Application Priority Data
Dec. 18, 2015   (FR) ...................... 15 62756

(51) Int. Cl.
| | |
|---|---|
| *B01J 31/24* | (2006.01) |
| *C07C 2/36* | (2006.01) |
| *B01J 31/02* | (2006.01) |
| *B01J 31/18* | (2006.01) |
| *B01J 31/22* | (2006.01) |
| *B01J 31/14* | (2006.01) |
| *C10G 50/00* | (2006.01) |
| *C07C 11/08* | (2006.01) |
| *C07C 11/10* | (2006.01) |
| *C07C 11/107* | (2006.01) |

(52) U.S. Cl.
CPC ....... *B01J 31/2404* (2013.01); *B01J 31/0204* (2013.01); *B01J 31/0244* (2013.01); *B01J 31/0267* (2013.01); *B01J 31/143* (2013.01); *B01J 31/181* (2013.01); *B01J 31/2208* (2013.01); *B01J 31/24* (2013.01); *C07C 2/36* (2013.01); *C10G 50/00* (2013.01); *B01J 2231/20* (2013.01); *B01J 2531/847* (2013.01); *C07C 11/08* (2013.01); *C07C 11/10* (2013.01); *C07C 11/107* (2013.01); *C07C 2531/14* (2013.01); *C07C 2531/24* (2013.01); *C10G 2300/1092* (2013.01); *C10G 2400/20* (2013.01); *C10G 2400/22* (2013.01)

(58) Field of Classification Search
CPC ......... C07C 2/36; C07C 11/107; C07C 11/10; C07C 11/08; C07C 2531/24; C07C 2531/14; B01J 31/2404; B01J 31/0204; B01J 31/0244; B01J 31/0267; B01J 31/143; B01J 31/24; B01J 31/2208; B01J 31/181; B01J 2531/847; B01J 2231/20; C10G 50/00; C10G 2400/22; C10G 2300/1092; C10G 2400/20
See application file for complete search history.

(56) References Cited

U.S. PATENT DOCUMENTS

| | | | |
|---|---|---|---|
| 5,166,114 A | 11/1992 | Wu | |
| 10,300,473 B2* | 5/2019 | Breuil | .............. B01J 31/143 |
| 2002/0173685 A1* | 11/2002 | Brown | ............. B01J 31/185 |
| | | | 585/502 |
| 2013/0066128 A1* | 3/2013 | Breuil | ............. B01J 31/1815 |
| | | | 585/511 |
| 2015/0306588 A1* | 10/2015 | Boulens | ............. C07C 2/34 |
| | | | 556/21 |
| 2015/0306589 A1* | 10/2015 | Boulens | ............ B01J 31/2295 |
| | | | 556/20 |

OTHER PUBLICATIONS

R. Ceder: Catalytic dimerization of ethylene to 1-butene by square-planar nickel complexes Journal of Molecular Catalysis, vol. 68, Issue 1, Aug. 15, 1991, pp. 23-31.
International Search Report PCT/EP2016/080737 dated May 3, 2017.

* cited by examiner

*Primary Examiner* — Ali Z Fadhel
(74) *Attorney, Agent, or Firm* — Millen, White, Zelano & Branigan, PC; Ryan Pool

(57) ABSTRACT

The invention concerns a catalytic composition comprising: at least one nickel precursor with an oxidation number of (+II), at least one phosphine ligand with formula $PR^1R^2R^3$ in which the groups $R^1$, $R^2$ and $R^3$, which may be identical or different and which may or may not be bonded together, and at least one Lewis base, said composition having a molar ratio of the phosphine ligand to the nickel precursor of less than or equal to 5 and a molar ratio of the Lewis base and phosphine ligand together to the nickel precursor of greater than or equal to 5.

16 Claims, No Drawings

CATALYTIC COMPOSITION COMPRISING NICKEL, A PHOSPHINE-TYPE LIGAND AND A LEWIS BASE, AND USE THEREOF IN AN OLEFIN OLIGOMERISATION METHOD

The present invention relates to a novel nickel-based composition and to its use as a catalyst in chemical transformation reactions, and in particular in a process for the oligomerization of an olefinic feed.

The invention also relates to a process for the oligomerization of a feed of olefins, comprising bringing said feed into contact with the nickel-based composition in accordance with the invention, and in particular to a process for the dimerization of ethylene into 1-butene in particular which employs said nickel-based composition in accordance with the invention.

PRIOR ART

The transformation of ethylene using a homogeneous nickel catalyst has been studied since 1950. This research led to the development and commercialization of a variety of processes.

The development of catalytic systems which are capable of dimerizing ethylene into butenes involves selecting a suitable metal and ligands. Among the existing systems, several nickel-based catalytic systems using phosphine type ligands have been developed.

Thus, the U.S. Pat. No. 5,237,118 B describes a process for the oligomerization of ethylene employing a catalytic composition comprising a nickel compound with oxidation number zero, and a phosphine ligand in variable proportions with respect to the nickel compound. That patent also describes the use of a fluorine-containing organic acid for carrying out an oligomerization process. Apart from phosphine, that patent does not describe the presence of a Lewis base in the catalytic composition.

The U.S. Pat. No. 4,242,531 B describes a process for the dimerization of olefins and employs a catalytic system based on chlorine-containing nickel compounds with an oxidation number of +2 and an activator of the halogenated alkylaluminium type. That patent is aimed at the production of 2-butenes and apart from phosphine, it does not describe the presence of a Lewis base in the catalytic system.

The patent FR 1 547 921 describes a catalytic composition based on a nickel halide and phosphine which necessitates a prior reduction of the composition with a view to preparing the active catalyst. Apart from phosphine, that patent does not describe the presence of a Lewis base in the catalytic composition. The butenes yields are of the order of 63% of C4, including 3% of 1-butenes.

The patent FR 1 588 162 describes a process for the dimerization of C2 to C4 olefins employing a catalytic system comprising a nickel compound and a phosphine, and in particular alkyl halides, with yields of butenes of the order of 80%. Apart from phosphine, that patent does not describe the presence of a Lewis base in the catalytic system. That patent is aimed at the production of 2-butenes.

There is still a need for the development of novel catalytic compositions which perform better in terms of yield and selectivity for the oligomerization of olefins, in particular for the dimerization of ethylene, in particular to form 1-butene.

During the course of its research, the Applicant has developed a novel catalytic composition comprising a nickel precursor with an oxidation number of (+II), at least one phosphine ligand and a Lewis base, such that the molar ratio of the phosphine ligand to the nickel precursor is less than or equal to 5 and the molar ratio of the Lewis base and phosphine ligand together to the nickel precursor is greater than or equal to 5. The catalytic composition may comprise at least one activating agent. It has surprisingly been shown that compositions of this type have interesting catalytic properties. In particular, these compositions have a good yield/catalytic selectivity ratio in the oligomerization of olefins, more precisely in the selective dimerization of ethylene to 1-butene.

One aim of the invention is to provide a novel nickel-based composition. Another aim of the invention is to propose a novel catalytic system comprising said composition for chemical transformation reactions, in particular for the oligomerization of olefins, especially the dimerization of ethylene to 1-butene.

DETAILED DESCRIPTION OF THE INVENTION

Composition in Accordance with the Invention

The catalytic composition in accordance with the invention comprises:
- at least one nickel precursor with an oxidation number of (+II),
- at least one phosphine ligand with formula $PR^1R^2R^3$ in which the groups $R^1$, $R^2$ and $R^3$, which may be identical or different, and which may or may not be bonded together, are selected from
  aromatic groups which may or may not be substituted and which may or may not contain heteroelements,
  and/or from hydrocarbyl groups, which may or may not be cyclic, which may or may not be substituted and which may or may not contain heteroelements,
- and at least one Lewis base, said composition having a molar ratio of the phosphine ligand to the nickel precursor of less than or equal to 5 and a molar ratio of the Lewis base and phosphine ligand together to the nickel precursor of greater than or equal to 5.

Advantageously in accordance with the invention, the catalytic composition comprises at least one phosphine ligand of formula $PR^1R^2R^3$ in which the groups $R^1$, $R^2$ and $R^3$ are identical.

The aromatic groups $R^1$, $R^2$ and $R^3$ of the phosphine ligand $PR^1R^2R^3$ are preferably selected from the group formed by the following groups: phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bis-naphthyl, pyridyl, bisphenyl, furanyl and thiophenyl.

The hydrocarbyl groups $R^1$, $R^2$ and $R^3$ of the phosphine ligand $PR^1R^2R^3$ advantageously contain 1 to 20 carbon atoms, preferably 2 to 15 carbon atoms, more preferably between 3 and 10 carbon atoms. Preferably, the hydrocarbyl groups $R^1$, $R^2$ and $R^3$ of the phosphine ligand $PR^1R^2R^3$ are selected from the group formed by the following groups: methyl, ethyl, propyl, isopropyl, n-butyl, tert-butyl, cyclopentyl, cyclohexyl, benzyl and adamantyl, preferably from the group formed by the following groups: isopropyl, n-butyl, cyclopentyl and cyclohexyl.

In accordance with the invention, the nickel precursor in accordance with the invention has an oxidation number of +II. It is preferably selected from nickel(II) chloride; nickel (II) (dimethoxyethane) chloride; nickel(II) bromide; nickel (II) (dimethoxyethane) bromide; nickel(II) fluoride; nickel (II) iodide; nickel(II) sulphate; nickel(II) carbonate; nickel (II) dimethylglyoxime; nickel(II) hydroxide; nickel(II) hydroxyacetate; nickel(II) oxalate; nickel(II) carboxylates selected from the group formed by nickel(II) 2-ethylhexanoate, nickel(II) acetate, nickel(II) trifluoroacetate, nickel(II) triflate, nickel(II) acetylacetonate, nickel(II) hexafluoroacetylacetonate, nickel(II) phenates; allylnickel(II) chloride; allylnickel(II) bromide; the dimer of methallylnickel(II) chloride; allylnickel(II) hexafluorophosphate; methallylnickel(II) hexafluorophosphate; biscyclopentadienyl nickel (II); bisallyl nickel(II) and bismethallyl nickel(II); in their hydrated form or otherwise, used alone or as a mixture.

Preferably, the nickel precursor is selected from nickel(II) sulphate; nickel(II) carbonate; nickel(II) dimethylglyoxime; nickel(II) hydroxide, nickel(II) hydroxyacetate; nickel(II) oxalate; nickel(II) carboxylates selected from the group formed by nickel(II) 2-ethylhexanoate, nickel(II) acetate, nickel(II) trifluoroacetate, nickel(II) triflate, nickel(II) acetylacetonate, nickel(II) hexafluoroacetylacetonate, nickel(II) phenates; allylnickel(II) hexafluorophosphate; methallylnickel(II) hexafluorophosphate; biscyclopentadienyl nickel (II); bisallyl nickel(II) and bismethallyl nickel(II); in their hydrated form or otherwise, used alone or as a mixture.

The catalytic composition in accordance with the invention comprises a Lewis base. In the context of the present invention, the term "Lewis base" means any chemical entity which does not contain phosphorus wherein one constituent has one or more pairs of free or non-bonding electrons. In particular, the Lewis bases in accordance with the invention correspond to any ligand comprising an oxygen or nitrogen atom having a pair of free or non-bonding electrons, or a π double bond which is capable of forming a $\eta^2$ if type coordination with the nickel. According to the invention, the term Lewis base refers to a Lewis base containing an oxygen atom or a nitrogen atom.

The Lewis base in accordance with the invention is preferably selected from diethylether, methyl tert-butylether, tetrahydrofuran, 1,4-dioxane, isoxazole, pyridine, pyrazine and pyrimidine. Preferably, the Lewis base is selected from tetrahydrofuran, 1,4-dioxane and pyridine.

The composition in accordance with the invention may also comprise an activating agent selected from the group formed by chlorine- and bromine-containing compounds of hydrocarbylaluminium, used alone or as a mixture.

Advantageously, said activating agent is selected from the group formed by methylaluminium dichloride ($MeAlCl_2$), ethylaluminium dichloride ($EtAlCl_2$), ethylaluminium sesquichloride ($Et_3Al_2Cl_3$), diethylaluminium chloride ($Et_2AlCl$), diisobutylaluminium chloride ($iBu_2AlCl$), isobutylaluminium dichloride ($iBuAlCl_2$), used alone or as a mixture.

In accordance with the invention, the molar ratio of the phosphine ligand to the nickel precursor is less than or equal to 5 and preferably in the range 2 to 5, preferably equal to 2, 3, 4 or 5.

In accordance with the invention, the molar ratio of the Lewis base and phosphine ligand together to the nickel precursor is greater than or equal to 5 and preferably in the range 5 to 30, preferably in the range 5 to 25, preferably in the range 5 to 20, preferably in the range 5 to 15. Preferably, the molar ratio of the Lewis base and phosphine ligand together to the nickel precursor is greater than or equal to 6 and preferably in the range 6 to 30, preferably in the range 6 to 25, preferably in the range 6 to 20, preferably in the range 6 to 15.

Advantageously, the molar ratio of the activating agent to the phosphine ligand is greater than or equal to 1, preferably greater than or equal to 1.5, preferably greater than or equal to 2, when the activating agent is present in the composition.

In accordance with the invention, the molar ratio of the activating agent to the nickel precursor is preferably greater than or equal to 5, more preferably greater than or equal to 6, and preferably less than or equal to 30, preferably less than or equal to 25, more preferably less than or equal to 20.

The molar ratios mentioned in the present invention, in particular with respect to the nickel precursor, are understood to be and expressed with respect to the number of moles of nickel supplied to the catalytic composition.

The compositions in accordance with the invention may also optionally comprise a solvent. A solvent selected from organic solvents and in particular from alcohols, chlorine-containing solvents and saturated, unsaturated, aromatic or non-aromatic, cyclic or non-cyclic hydrocarbons may be used. Preferably, the solvent is selected from hexane, cyclohexane, methylcyclohexane, heptane, butane or isobutane or any other hydrocarbon cut with boiling points of more than 70° C., preferably in the range 70° C. to 200° C. and more preferably in the range 90° C. to 180° C., the monoolefins or diolefins preferably containing 4 to 20 carbon atoms, cycloocta-1,5-diene, benzene, toluene, ortho-xylene, mesitylene, ethylbenzene, dichloromethane, chlorobenzene, methanol, ethanol, pure or as a mixture, and ionic liquids. In the case in which the solvent is an ionic liquid, it is advantageously selected from the ionic liquids described in patents U.S. Pat. No. 6,951,831 B2 and FR 2 895 406 B1.

Use of the Composition in Accordance with the Invention

The compositions in accordance with the invention may be used as a catalyst in a chemical transformation reaction such as the hydrogenation reaction, hydroformylation reaction, cross-coupling or the oligomerization of olefins. In particular, these compositions are used in a process for the oligomerization of a feed of olefins advantageously containing 2 to 10 carbon atoms.

Preferably, the oligomerization process is a process for the dimerization of ethylene, in particular to form 1-butene.

The oligomerization process in accordance with the invention is advantageously operated in the presence of a solvent.

The solvent for the oligomerization process may be selected from organic solvents, and preferably from chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, dichloromethane, chlorobenzene, pure or as a mixture, and ionic liquids. In the case in which said reaction solvent is an ionic liquid, it is advantageously selected from the ionic liquids described in the patents U.S. Pat. No. 6,951,831 B2 and FR 2 8954 06 B1.

Oligomerisation is defined as the transformation of a monomer unit into a compound or mixture of compounds with general formula $C_pH_{2p}$, where $4 \leq p \leq 80$, preferably $4 \leq p \leq 50$, more preferably $4 \leq p \leq 26$ and still more preferably $4 \leq p \leq 14$.

The olefins used in the oligomerization process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) or any other oil cut such as those found in "cuts" obtained from oil refining or petrochemicals processes, such as catalytic cracking or steam cracking.

Preferably, the olefin used in the oligomerization process is ethylene.

Said olefins may be obtained from non-fossil resources such as biomass. As an example, the olefins used in the oligomerization process in accordance with the invention may be produced from alcohols, in particular by dehydration of the alcohols.

The concentration of nickel in the catalytic solution is advantageously in the range $1 \times 10^{-8}$ to 1 mol/L, and preferably in the range $1 \times 10^{-6}$ to $1 \times 10^{-2}$ mol/L.

The oligomerization process is advantageously operated at a total pressure in the range between atmospheric pressure and 20 MPa, preferably in the range 0.1 to 8 MPa, and at a temperature in the range −40° C. to 250° C., preferably in the range −20° C. to 150° C.

The heat generated by the reaction may be eliminated using any means known to the person skilled in the art.

The oligomerization process may be carried out in a closed system, a semi-open system or continuously, with one or more reaction stages. Vigorous stirring is advantageously undertaken in order to ensure good contact between the reagent or reagents and the catalytic system.

The oligomerization process may be carried out batch-wise. In this case, a selected volume of the solution comprising the composition in accordance with the invention is introduced into a reactor which is preferably provided with the usual stirring, heating and cooling devices.

The oligomerization process may also be carried out continuously. In this case, the solution comprising the composition in accordance with the invention is injected into a reactor in which the olefin is reacted, preferably with control of the temperature.

The catalytic composition is destroyed using any usual means known to the person skilled in the art, then the reaction products as well as the solvent are separated, for example by distillation. The olefin which has not been transformed may be recycled to the reactor.

The products of the present process may, for example, find application as components of fuels for automobiles, as feeds in a hydroformylation process for the synthesis of aldehydes and alcohols, as components for the chemical, pharmaceutical or perfumery industry, and/or as feeds in a metathesis process for the synthesis of propylene and/or as a feed for a process for the production of butadiene via an oxidizing dehydrogenation, or via a step for metallic catalysis, for example.

The following examples illustrate the invention without limiting its scope.

EXAMPLES

Implementation of the Catalytic Test:

The reactor was initially vacuum dried and placed under an atmosphere of ethylene. 93 mL of cyclohexane was introduced into the reactor under an atmosphere of ethylene. 6 mL of a solution containing the nickel precursor Ni(2-ethylhexanoate)$_2$, denoted Ni(2-EH)$_2$ (10 or 20 μmol), and tricyclohexylphosphine PCy$_3$ (2 or 5 molar equivalents with respect to the nickel) and pyridine or tetrahydrofuran (5, 8 or 10 molar equivalents with respect to nickel) were then introduced into the reactor. Between 1 and 2 g of ethylene was then dissolved in the reactor, stirring was commenced and the temperature was programmed to 40° C. After degassing the reactor, the temperature was programmed to 50° C. (test temperature). 1 mL of a solution of ethylaluminium dichloride (15 molar equivalents with respect to nickel) was then introduced. The reactor was pressurized to the test pressure (2 MPa). The ethylene consumption was monitored until 200 g of ethylene had been introduced or the reaction had run for 60 minutes. The ethylene supply was then cut off. The gas phase was quantified and qualified by gas chromatography (GC); the liquid phase was weighed, neutralized and qualified by GC.

Catalytic Tests

Examples 1-3

Comparative Examples

| Ex. | Ligand (eq.) | Lewis base (eq.) | Time (min) | Activity ($10^3$ g/ (g · h)) | % C4* | % C6 | % C8$^+$ | % 1-C4** |
|---|---|---|---|---|---|---|---|---|
| 1 | PCy$_3$ (2) | — | 20 | 199 | 87.8 | 10.9 | 1.3 | 53.4 |
| 2 | — | Pyridine (10) | 60 | — | — | — | — | — |
| 3 | — | THF (10) | 60 | — | — | — | — | — |

$n_{Ni(2-EH)2}$ = 10 μmol, 15 eq. EtAlCl$_2$, 2 MPa, 50° C., cyclohexane (100 mL).
*Yield of C4 corresponding to percentage by weight of the C4 cut formed in the products.
**Percentage of 1-C4 in the C4 cut.

Examples 4-7

Examples in Accordance with the Invention

| Ex. | Ligand (eq) | Lewis base (eq.) | (Ligand + Lewis base)/ nickel | Time (min) | Activity ($10^3$ g/ (g · h)) | % C4* | % C6 | % C8$^+$ | % 1-C4** |
|---|---|---|---|---|---|---|---|---|---|
| 4 | PCy$_3$ (2) | Pyridine (8) | 10 | 30 | 297 | 90.2 | 8.9 | 0.9 | 62.6 |
| 5 | PCy$_3$ (5) | Pyridine (5) | 10 | 18 | 510 | 90.0 | 8.9 | 1.1 | 59.7 |
| 6 | PCy$_3$ (5) | Pyridine (10) | 15 | 60 | 44 | 95.1 | 4.7 | 0.2 | 94.2 |
| 7 | PCy$_3$ (5) | THF (5) | 10 | 29 | 295 | 92.8 | 6.7 | 0.5 | 89.6 |

$n_{Ni(2-EH)2}$ = 20 μmol, 15 eq. EtAlCl$_2$, 2 MPa, 50° C., cyclohexane (100 mL).
*Yield of C4 corresponding to percentage by weight of the C4 cut formed in the products.
**Percentage of 1-C4 in the C4 cut.

It can be seen that the catalytic compositions in accordance with the invention can be used to obtain a butenes cut (C4) in a yield of at least 90.0% and a selectivity for 1-butene (1-C4) of at least 59.7%.

The invention claimed is:
1. A catalytic composition comprising:
   a at least one nickel compound with an oxidation number of (+II),
   b at least one phosphine ligand with formula PR$^1$R$^2$R$^3$, in which the groups R$^1$, R$^2$ and R$^3$, which may be identical or different, and which may or may not be bonded together, are selected from:
      aromatic groups which may or may not be substituted and which may or may not contain heteroelements, and/or from hydrocarbyl groups, which may or may not be cyclic, which may or may not be substituted and which may or may not contain heteroelements, c an activating agent selected from the group formed by chlorine- and bromine-containing compounds of hydrocarbyl aluminum, used alone or as a mixture, and
d at least one Lewis base,
wherein said composition having a molar ratio of the phosphine ligand to the nickel compound of less than or equal to 5, a molar ratio of the Lewis base and phosphine ligand together to the nickel compound comprised of between 5 to 30, and a molar ratio of the activating agent to the nickel compound of greater than or equal to 6.

2. The composition as claimed in claim 1, in which the molar ratio of the phosphine ligand to the nickel compound is in the range 2 and 5.

3. The composition as claimed in claim 1, in which the nickel compound is selected from nickel(II) chloride; nickel (II) (dimethoxyethane) chloride; nickel(II) bromide; nickel (II) (dimethoxyethane) bromide; nickel(II) fluoride; nickel (II) iodide; nickel(II) sulphate; nickel(II) carbonate; nickel (II) dimethylglyoxime; nickel(II) hydroxide; nickel(II) hydroxyacetate; nickel(II) oxalate; nickel(II) carboxylates selected from the group formed by nickel(II) 2-ethylhexanoate; nickel(II) acetate; nickel(II) trifluoroacetate; nickel(II) triflate; nickel(II) acetylacetonate; nickel(II) hexafluoroacetylacetonate; nickel(II) phenates; allylnickel(II) chloride; allylnickel(II) bromide; the dimer of methallylnickel(II) chloride; allylnickel(II) hexafluorophosphate; methallylnickel(II) hexafluorophosphate; biscyclopentadienyl nickel (II); bisallyl nickel(II) and bismethallyl nickel(II); in their hydrated form or otherwise; used alone or as a mixture.

4. The composition as claimed in claim 1, in which the nickel compound is selected from nickel(II) sulphate; nickel (II) carbonate; nickel(II) dimethylglyoxime; nickel(II) hydroxide; nickel(II) hydroxyacetate; nickel(II) oxalate; nickel(II) carboxylates selected from the group formed by nickel(II) 2-ethylhexanoate; nickel(II) acetate; nickel(II) trifluoroacetate; nickel(II) triflate; nickel(II) acetylacetonate; nickel(II) hexafluoroacetylacetonate; nickel(II) phenates; allylnickel(II) hexafluorophosphate; methallylnickel(II) hexafluorophosphate; nickel(II); bisallyl nickel(II) and bismethallyl nickel(II); in their hydrated form or otherwise, used alone or as a mixture.

5. The composition as claimed in claim 1, in which the groups IV, $R^2$ and $R^3$ of said phosphine ligand are identical.

6. The composition as claimed in claim 1, in which the aromatic groups $R^1$, $R^2$ and $R^3$ of the phosphine ligand $PR^1R^2R^3$ are selected from the group formed by the following groups: phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl and thiophenyl.

7. The composition as claimed in claim 1, in which the hydrocarbyl groups $R^1$, $R^2$ and $R^3$ of the phosphine ligand $PR^1R^2R^3$ contain 1 to 20 carbon atoms.

8. The composition as claimed in claim 7, in which the hydrocarbyl groups IV, $R^2$ and $R^3$ of the phosphine ligand $PR^1R^2R^3$ are selected from the group formed by the following groups: methyl, ethyl, propyl, isopropyl, n-butyl, tert-butyl, cyclopentyl, cyclohexyl, benzyl, adamantyl.

9. The composition as claimed in claim 1, in which the Lewis base is selected from diethylether, methyl tert-butylether, tetrahydrofuran, 1,4-dioxane, isoxazole, pyridine, pyrazine and pyrimidine.

10. The composition as claimed in claim 1, in which the said activating agent is selected from the group formed by methylaluminium dichloride ($MeAlCl_2$), ethylaluminium dichloride ($EtAlCl_2$), ethylaluminium sesquichloride ($Et_3Al_2Cl_3$), diethylaluminium chloride ($Et_2AlCl$), diisobutylaluminium chloride ($iBu_2AlCl$) and isobutylaluminium dichloride ($iBuAlCl_2$), used alone or as a mixture.

11. The composition as claimed in claim 1, in which the molar ratio of the activating agent to the phosphine ligand is greater than or equal to 1.

12. A process for the oligomerization of a feed of olefins, comprising contacting said feed of olefins with the catalytic composition of claim 1 to form a product.

13. The process as claimed in claim 12, in which the feed comprises olefins containing in the range 2 to 10 carbon atoms.

14. The process as claimed in claim 12, carried out in a closed system, in a semi-open system, continuously or batchwise.

15. The process as claimed in claim 12, in which said process is a process for the dimerization of ethylene.

16. The process of claim 12 further comprising:
adding said product to a fuel for automobiles.

* * * * *